United States Patent [19]

Kaul

[11] 4,033,963
[45] July 5, 1977

[54] NAPHTHOQUINONE DERIVATIVES

[75] Inventor: Bansi Lal Kaul, Basel, Switzerland

[73] Assignee: Sandoz Ltd., Basel, Switzerland

[22] Filed: Sept. 15, 1975

[21] Appl. No.: 613,336

Related U.S. Application Data

[62] Division of Ser. No. 411,086, Oct. 30, 1973, Pat. No. 3,931,163.

[52] U.S. Cl. .................. 260/256.4 C; 260/248 CS; 260/249.5; 260/249.8; 260/249.9; 260/256.4 R; 260/256.4 N; 260/256.5 R
[51] Int. Cl.$^2$ ........................... C07D 471/04
[58] Field of Search ............ 260/256.4 R, 256.4 C, 260/256.4 N

[56] References Cited

UNITED STATES PATENTS

| | | | |
|---|---|---|---|
| 3,413,302 | 11/1968 | Demler | 260/296 |
| 3,931,163 | 1/1976 | Kaul | 260/256.4 C |

FOREIGN PATENTS OR APPLICATIONS 1,392,872 2/1965 France

*Primary Examiner*—Donald G. Daus
*Assistant Examiner*—James H. Turnipseed
*Attorney, Agent, or Firm*—Gerald D. Sharkin; Richard E. Vila; Joseph J. Borovian

[57] ABSTRACT

The present invention relates to naphthoquinone derivatives of formula I,

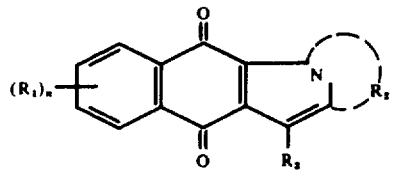

in which
R$_1$ signifies a halogen atom, a nitro group or an unsubstituted or substituted alkoxy or amino group,
R$_2$ signifies the atoms necessary to form an unsaturated ring system, which ring system has 1 or 2 nuclei and is unsubstituted or substituted,
R$_3$ signifies an unsubstituted or substituted 5-triazinyl or pyrimidyl radical, and
n is 0, 1 or 2,
which compounds are free from sulphonic acid groups are useful as pigments or disperse dyes.

4 Claims, No Drawings

NAPHTHOQUINONE DERIVATIVES

This is a division of application Ser. No. 411,086 filed Oct. 30, 1973, which issued as U.S. Pat. No. 3,931,163 on Jan. 6, 1976.

The invention relates to naphthoquinone derivatives.

Accordingly, the invention provides compounds of formula I,

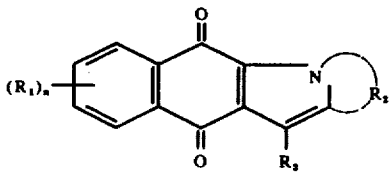

in which
R$_1$ signifies a halogen atom, a nitro group or an unsubstituted or substituted alkoxy or amino group,
R$_2$ signifies the atoms necessary to form an unsaturated ring system, which ring system has 1 or 2 nuclei and is unsubstituted or substituted,
R$_3$ signifies an unsubstituted or substituted s-triazinyl or pyrimidyl radical, and $n$ is 0, 1 or 2, which compounds are free from sulphonic acid groups.

In the compounds of formula I, where R$_1$ signifies a substituted alkoxy radical, such radical is preferably substituted by a chlorine or bromine atom or by a hydroxy or alkoxy group. Where R$_1$ signifies an unsubstituted or substituted amino group, such group is preferably of formula

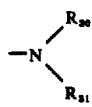

in which
each of R$_{30}$ and R$_{31}$, which may be the same or different, signifies a hydrogen atom; an unsubstituted alkyl or phenyl radical; an alkyl radical substituted by a chlorine or bromine atom or a hydroxy or alkoxy group, preferably by a hydroxy group; a phenyl radical substituted by up to three substituents selected from the group consisting of chlorine and bromine atoms, hydroxy and alkoxy groups, preferably chlorine atoms and more preferably, such phenyl is mono-substituted; or a group of formula

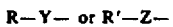

R—Y— or R'—Z— in which
R signifies an unsubstituted alkyl or phenyl radical or an alkyl or phenyl radical substituted by chlorine, bromine, hydroxy or alkoxy, preferably an unsubstituted alkyl or phenyl radical,
Y signifies a radical of formula —O—CO— or —SO$_2$—,
R' signifies a hydrogen atom or has one of the significances of R, and
Z signifies a radical of formula —CO—, —NR'CO— or —NR'SO$_2$— in which R' is as defined above, with the proviso that when one of R$_{30}$ or R$_{31}$ is a phenyl, substituted phenyl or a group of the formula R—Y— or R'—Z—, as defined above, the other has a significance other than phenyl, substituted phenyl, R—Y— or R'—Z—, any alkoxy groups or alkyl or alkoxy moeties contain 1 to 4 carbon atoms.

Preferred compounds of formula I, are those where $n$ is 0.

In the compounds of formula I, R$_2$ preferably signifies a radical of formula P or Q,

—CH=CH—CH=CH—    P

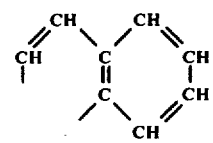

which radicals are unsubstituted or are substituted by up to three substituents selected from the group consisting of halogen atoms; unsubstituted C$_{1-4}$ alkyl or alkoxy radicals; (C$_{1-4}$) alkyl and alkoxy radicals substituted by a chlorine or bromine atom, a hydroxy or (C$_{1-4}$) alkoxy group; phenoxy and nitro groups; groups of formula R—Y—, R—Y—O—, R—Y—NH—, R'—Z, R'—Z—O— and R'—Z—NH— in which R, R', Z and Y are as defined above, more preferably, such radicals are unsubstituted or mono-substituted.

As examples of the groups of formulae R—Y—, R—Y—O—, R—Y—NH—, R'—Z—, R'—Z—O—, and R'—Z—NH— may be given alkylaminocarbonyl, alkylaminocarbonyloxy, alkylaminocarbonylamino, aminocarbonyl, aminocarbonyloxy, aminocarbonylamino, alkylcarbonyl, alkylcarbonyloxy, alkylcarbonylamino, dialkylaminocarbonyl, dialkylaminocarbonyloxy, dialkylaminocarbonylamino, phenylaminocarbonyl, phenylaminocarbonyloxy, phenylaminocarbonylamino, alkoxycarbonyl, alkoxycarbonylamino, alkoxycarbonyloxy, benzoyl, benzoyloxy and benzoylamino groups; all alkyl and alkoxy groups and moeties in such groups contain 1 to 4 carbon atoms.

Particularly preferred substituents on the radicals of R$_2$ include chlorine, bromine, alkyl, alkoxy, aminocarbonyl, alkylaminocarbonyl, dialkylaminocarbonyl, phenylaminocarbonyl or alkoxycarbonyl, which alkyl and alkoxy groups or moeties in such groups contain 1 to 4 carbon atoms.

In the compounds of formula I, where R$_3$ signifies a substituted pyrimidyl or s-triazinyl radical, such pyrimidyl radical is substituted by up to 3 substituents, such s-triazinyl radical is substituted by up to 2 substituents, which substituents are selected from the group consisting of fluorine, chlorine and bromine atoms; unsubstituted alkyl and alkoxy groups; alkyl and alkoxy groups substituted by a chlorine or bromine atom or a hydroxy or alkoxy group; hydroxy and phenoxy groups; and groups of the formula

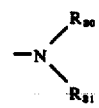

in which
R$_{30}$ and R$_{31}$ are as defined above, any alkyl or alkoxy substituents or moieties in such substituents contain 1 to 4 carbon atoms.

Preferably, the substituents on the s-triazinyl radical or on the pyrimidyl radical are selected from the group consisting of hydroxyl, $(C_{1-4})$alkoxy, amino, $(C_{1-4})$alkylamino, $(C_{1-4})$dialkylamino, substituted $(C_{1-4})$ dialkylamino, phenylamino and mono-substituted phenylamino groups. Preferred compounds are those where the pyrimidyl or s-triazinyl radicals are substituted.

All alkyl and alkoxy radicals or moieties in the compounds of formula I preferably contain 1 to 4 carbon atoms.

Preferred compounds of formula I, are those of formula Ia,

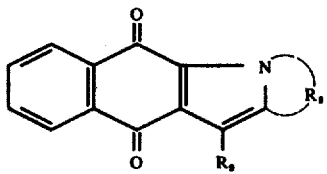

in which
R_8 signifies a radical of formula P or Q, which radicals are unsubstituted or are substituted by a chlorine or bromine atom, a methyl, methoxy aminocarbonyl, methylaminocarbonyl, ethylaminocarbonyl, dimethylaminocarbonyl, diethylaminocarbonyl, phenylaminocarbonyl, methoxycarbonyl or ethoxycarbonyl, and
R_9 signifies an s-triazinyl or pyrimidyl radical substituted by up to two and up to three substituents respectively, which substituents are selected from the group consisting of hydroxyl, methoxy, ethoxy, amino, methylamino, ethylamino, dimethylamino, diethylamino, di-hydroxyethylamino, phenylamino or mono-chlorophenylamino groups.

Even more preferred compounds are those of formula Ib,

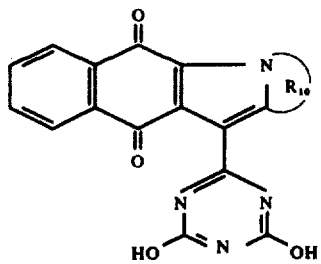

in which
R_{10} signifies a radical of formula P, which is unsubstituted or substituted by a chlorine atom, a methyl, aminocarbonyl, methoxycarbonyl or ethoxycarbonyl group.

The invention also provides a process for the production of compounds of formula I, as defined above, characterised by
a. condensing one equivalent of a compound of formula II,

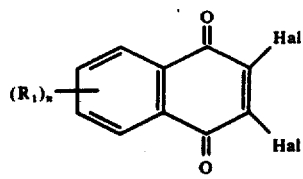

in which $R_1$ and $n$ are as defined above, and Hal signifies a chlorine or a bromine atom,
with one equivalent of a compound of formula III,

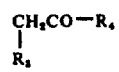

in which
$R_3$ is as defined above, and
$R_4$ signifies a phenoxy radical or an unsubstituted or substituted alkyl, alkoxy, phenyl or amino radical,
and with at least 3 equivalents of a compound of formula IV,

in which $R_2$ is as defined above, or
b. condensing a compound of formula II, as defined above, with a compound of formula VII,

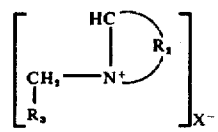

in which
$R_2$ and $R_3$ are as defined above, and X signifies a chlorine, bromine or iodine atom.

The condensation reaction of process (a) is preferably carried out in an inert organic solvent, for example, methanol, ethanol, propanol, butanol, dioxane, dimethylformamide, dimethylacetamide, benzene, toluene, xylene, nitrobenzene or the reaction may be carried out using a large excess of the compound of formula IV, as defined above, so that it acts as solvent. The reaction is suitably carried out at a temperature in the range of from 20° to 250° C, preferably from 50° to 200° C.

The condensation reaction of process b) is suitably carried out in an inert organic solvent, preferably in aliphatic or cyclic ethers with a boiling point of at least 50° C, for example, glycol dimethyl- or diethylether, tetrahydrofuran or dioxane. The reaction may be carried out at a temperature in the range of from 20° to 250°, preferably 50° to 200° C.

In the compounds of formula III, $R_4$ is preferably an alkoxy radical of 1 to 4 carbon atoms; an unsubstituted phenylamino radical; a phenylamino radical in which the phenyl nucleus is substituted by up to three substituents selected from the group consisting of methyl and methoxy groups, chlorine and bromine atoms; $(C_{1-4})$alkylamino groups and $(C_{1-2})$ dialkylamino groups.

The compounds of formula II and IV, as defined above, are known or may be produced according to known methods.

The compounds of formula III, as defined above, may be produced by hydrolytically splitting off an acyl radical of formula $R_4$—CO— or $R_4'$—CO— from a compound of formula VI,

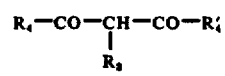

in which

R$_4$ and R$_3$ are as defined above, and

R$_4'$ has one of the significances of R$_4$, which process forms part of the present invention.

The splitting off of the acyl radical of formula R$_4$—CO— or R$_4'$—CO is conveniently effected in alkaline medium, preferably in the pH region of from 10 to 12 and in a polar solvent, for example, water; alcohols, such as ethanol, isopropanol, benzyl alcohol; glycols, such as ethylene glycol, propylene glycol, diethylene glycol; amides, such as dimethyl formamide, dimethylacetamide, hexamethyl phosphorous triamide; or dimethyl sulphoxide. The reaction may be carried out at a temperature between room temperature and the boiling point of the reaction mixture, preferably between 60° and 150° C.

The compounds of formula VI, as defined above, may be produced by condensing a compound of formula V,

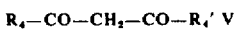

in which

R$_4$ and R$_4'$ are as defined above, with a compound of formula XI,

          XI in which

R$_3$ is as defined above, and

Hal signifies a chlorine or bromine atom.

The reaction of the compounds of formula V with the compounds of formula XI may be effected in a slightly to strongly alkaline medium, e.g. at pH values up to 12. When the reaction is carried out in strongly alkaline medium, the splitting of the acyl group occurs simultaneously with the condensation reaction.

Suitable solvents for the condensation reaction of a compound of formula V with a compound of formula XI are water, dioxane or acetone, or mixtures of these solvents. The reaction may be carried out at a temperature of from 0° to 50° C. Alkali metal carbonates or bicarbonates may be added to bind the nascent hydrogen halide.

If a compound of formula XI, in which R$_3$ signifies a s-triazinyl or pyrimidyl radical substituted by at least one halogen atom is employed, compounds of formula III may be formed, in which at least one of the halogen atoms on the R$_3$ nucleus has been substituted by any other substituent mentioned above as being present on the R$_3$ nucleus. This nucleophilic substitution may be effected before the condensation of the compound of formula XI with a compound of formula V, simultaneously with the cleavage of the acyl group, or after the compound of formula III containing at least one halogen atom on the R$_3$ nucleus has been obtained. The replacement of the halogen atoms with hydroxy, alkoxy, phenoxy or unsubstituted or substituted amino groups may take place under the same conditions as those described above for the cleavage of the R$_4$—CO— or R$_4'$—CO— group from the compound of formula VI, e.g. in strongly alkaline medium.

Compounds suitable for the introduction of hydroxy groups are, for example, alkali metal hydroxides, i.e. sodium, potassium or lithium hydroxide or alkaline earth metal oxides or hydroxides, i.e. magnesium oxide, calcium oxide or calcium hydroxide.

Compounds suitable for the introduction of alkoxy groups are, for example, alkali metal alcoholates, i.e. sodium or potassium alcoholate.

Similarly, phenoxy groups may be introduced by using alkali metal phenolates, e.g. sodium or potassium phenolate.

Amino groups may be introduced by using the corresponding amines alone or in the presence of alkali metal carbonates, bicarbonates or hydroxides. If more than one halogen is to be substituted, the substitution may be effected stepwise, the first group being introduced at a temperature of about 40° to 50° C with subsequent raising of the temperature to about 80° to 100° C to introduce the second group.

Preferably, the introduction of such groups takes place simultaneously with the cleavage of the R$_4$—CO— or R$_4'$—CO— group on the compound of formula VI containing halogen on the R$_3$ nucleus, to yield a compound of formula III on which the halogen on the R$_3$ nucleus has been substituted, such compounds of formula III may be in the form of alkali metal compounds.

To replace the halogen atoms on the R$_3$ nucleus with alkyl radicals, the halogen triazinyl or halogen pyrimidyl compounds are reacted with organo-metallic compounds, e.g. Grignard Reagents. The reaction is carried out in an anhydrous medium. Suitable solvents are, for example, benzene, toluene or xylene. The reaction temperature is gradually raised from room temperature to about 80° C with stirring.

The compounds of formula VII, as defined above, may be formed in the reaction mixture in situ by the addition of a compound of formula VIII,

          VIII in which

R$_3$ is as defined above, and

X signifies a chlorine, bromine or iodine atom, to a compound of formula IX,

          IX in which

R$_2$ is as defined above, or, by reacting a compound of formula IX, as defined above, with a compound of formula X,

          X in which

R$_3$ is as defined above.

In both reactions it is advisable to employ at least triple excess of the compound of formula IX or to employ the compound of formula IX exclusively as solvent. The reactions are suitably carried out at a temperature in the range of from 20° to 250° C, preferably from 50° to 200° C.

The invention still further provides compounds of formula III′,

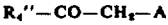          III′ in which $R_4''$ signifies an unsubstituted alkyl, alkoxy, phenoxy or phenyl radical; an alkyl radical substituted by a chlorine or bromine atom or a hydroxy or alkoxy group; a phenyl radical substituted by up to three substituents selected from the group consisting of chlorine and bromine atoms, hydroxy and alkoxy groups; or a radical of formula

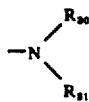

in which
$R_{30}$ and $R_{31}$ are as defined above, and
A signifies a radical of formula (a), (b), (c) or (d),

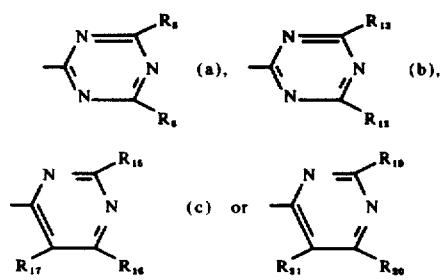

in which each of $R_5$, $R_6$, $R_{17}$, $R_{19}$, $R_{20}$ and $R_{21}$, which may be the same or different, signifies a hydrogen, fluorine, chlorine or bromine atom, a hydroxyl, alkyl, alkoxy, phenoxy or

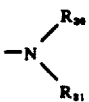

group, in which $R_{30}$ and $R_{31}$ are as defined above, each of $R_{12}$ and $R_{13}$, which may be the same or different, signifies a hydrogen atom, an alkoxy, phenoxy

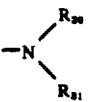

group in which $R_{30}$ and $R_{31}$ are as defined above, and each of $R_{15}$ and $R_{16}$, which may be the same or different, signifies a fluorine, chlorine or bromine atom, a hydroxyl, alkyl, alkoxy, phenoxy or

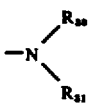

group, in which $R_{30}$ and $R_{31}$ are as defined above, with the proviso that (i) when A signifies a radical of formula (a), $R_4''$ signifies an unsubstituted or substituted alkyl or phenyl radical or a

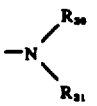

radical, as defined above, (ii) where A signifies a radical of formula (b), $R_4''$ signifies an alkoxy or phenoxy radical, (iii) where A signifies a radical of formula (c), $R_4''$ signifies an unsubstituted or substituted phenyl radical, and (iv) when A signifies a radical of formula (d), $R_4''$ has a significance other than an unsubstituted or substituted phenyl radical.

Thus, representative compounds of formula III' include those of formula IIIa', IIIb', IIIc' and IIId',

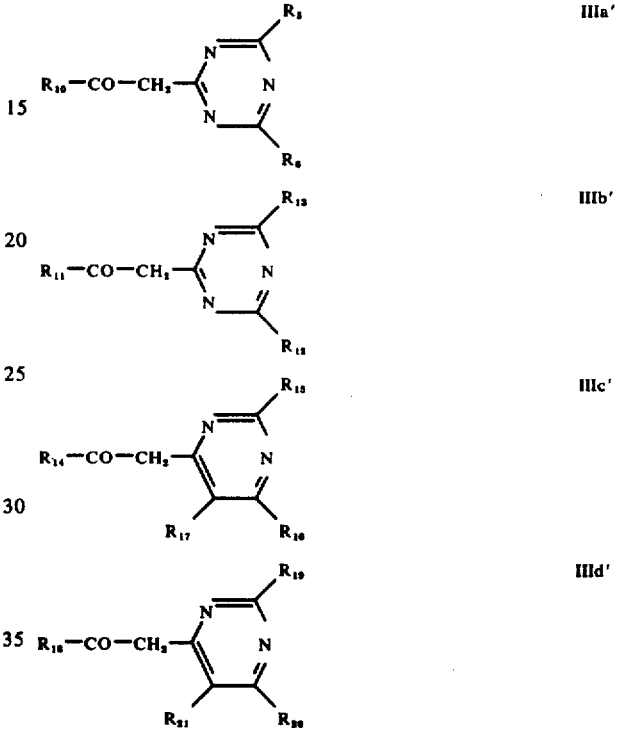

in which
$R_{10}$ signifies an unsubstituted alkyl or phenyl radical, an alkyl radical substituted by a chlorine or bromine atom or a hydroxy or alkoxy group, a phenyl radical substituted by up to three substituents selected from the group consisting of chlorine and bromine atoms, hydroxy and alkoxy groups, or a radical of formula

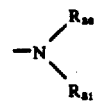

in which
$R_{30}$ and $R_{31}$ are as defined above,
$R_{11}$ signifies an alkoxy or phenoxy group, $R_{14}$ signifies an unsubstituted phenyl radical or a phenyl radical substituted by up to three substituents selected from the groups consisting of chlorine and bromine atoms, alkoxy and hydroxy groups,
$R_{18}$ signifies an alkoxy, phenoxy or

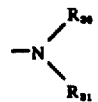

group, in which $R_{30}$ and $R_{31}$ are as defined above, an unsubstituted alkyl radical or an alkyl radical substituted by a chlorine or bromine atom, a hydroxyl or alkoxy group, and $R_5$, $R_6$, $R_{12}$, $R_{13}$, $R_{15}$, $R_{16}$, $R_{17}$, $R_{19}$, $R_{20}$ and $R_{21}$ are as defined above.

Preferably, all alkyl and alkoxy group or moieties in the compounds of formula III' contain 1 to 4 carbon atoms.

By the term 'halogen' as used herein, is to be understood chlorine, bromine, fluorine or iodine, in particular chlorine or bromine.

The compounds of formula I, as defined above, may be employed for pigmenting polymeric substrates in the mass. As examples of suitable substrates may be given viscose or cellulose acetate, polyethylene, polystyrene, polyvinyl chloride, rubber and artificial leather.

The compounds of formula I, as defined above, may also be converted into printing paste preparations and are suitable for pigmenting paper in the stock or for coating textiles.

The compounds of formula I, as defined above, may also be employed as disperse dyes, for which use they are preferably converted into dyeing preparations.

The compounds of formula I may be converted into dyeing preparations by known methods, for example, by grinding in the presence of dispersing agents and/or fillers, with or without subsequent vacuum or atomizer drying. The preparations are dispersed in a suitable amount of water for application by exhaust dyeing, pad dyeing or printing methods.

Thus, yet a further aspect of the present invention provides a process for dyeing or printing synthetic or semi-synthetic organic substrates of high molecular weight and hydrophobic character comprising applying thereto a dyeing or printing medium comprising A compound of formula I, as defined above, as dyeing or printing agent. As examples of suitable organic substrates may be given polyesters, cellulose diacetate, cellulose triacetate and synthetic polyamides. The substrates may be in loose fibre, yarn or fabric form.

Conventional dyeing or printing methods are employed, for example the process as described in French Patent No. 1,445,371.

The compounds of formula I, as defined above, where the $R_2$ nucleus is substituted, may be obtained as a mixture of positional isomers. The individual isomers may be prepared in conventional manner. However, such a mixture of positional isomers is suitable for the uses as indicated above for the compounds of formula I.

The following Examples serve to further illustrate the invention. In the Examples, all parts are by weight and all temperatures are in degrees Centigrade.

EXAMPLE 1

A mixture of 140.5 parts of 2-chloro-(4',6'-dihydroxy-1',3',5'-triazinyl)-acetylaminobenzene, 113.5 parts of 2,3-dichloro-1,4-naphthoquinone and 1000 parts of β-picoline is stirred for 30 minutes at 100° and for another 30 minutes at 140° to 145°. The dye settles out in insoluble form. On cooling to about 100°, the precipitated dye is filtered, washed with dimethyl formamide, ethanol, water, washed again with ethanol and finally dried at about 120°. The dye thus obtained agrees with the formula

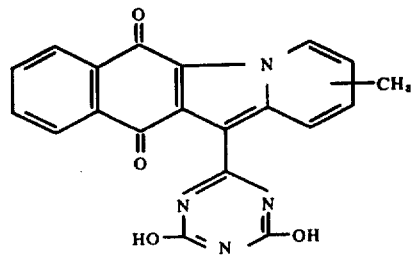

The values obtained by elementary analysis verify the empirical formula $C_{20}H_{12}N_4O_4$:

|          | C    | H   | N    | O    |
|----------|------|-----|------|------|
| Theory:  | 64.5 | 3.2 | 15.1 | 17.2 |
| Found:   | 64.2 | 3.3 | 15.2 | 16.8 |

In polyvinyl chloride the pigment gives dyeings of bluish red shade.

2-Chloro-(4',6'-dihydroxy-1',3',5'-triazinyl)-acetylaminobenzene can be produced as follows.

A solution of 396 parts of cyanuric chloride in 1000 parts of dioxane is slowly entered into 1000 parts of ice-water with stirring. The resulting mixture is combined very slowly over a period of about 40 minutes, with a mixture of 427 parts of 2-chloro-acetoacetylaminobenzene, 920 parts of water and 80 parts of sodium hydroxide at 0° to 5°. The mixture is stirred for another 30 minutes at the same temperature and the product is isolated by filtration. The precipitate is washed with ice-water, subsequently entered into 5000 parts of ethanol and boiled for 20 hours with stirring under reflux. On cooling to 20°, the precipitate is filtered, washed several times with hot water and dried at 100° under vacuum.

The compound thus obtained agrees with the formula

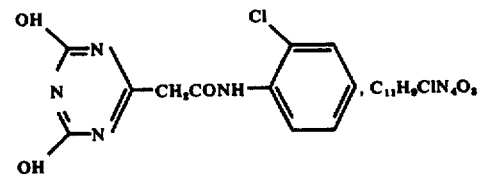

which is verified by elementary analysis:

|         | C    | H   | Cl   | N    | O    |
|---------|------|-----|------|------|------|
| Theory: | 47.1 | 3.2 | 12.6 | 20.0 | 17.1 |
| Found:  | 47.0 | 3.4 | 12.8 | 20.2 | 17.3 |

EXAMPLE 2

A mixture of 28.05 parts of 4-chloro-(4',6'-dihydroxy-1',3',5'-triazinyl)-acetylaminobenzene, 22.7 parts of 2,3-dichloro-1,4-naphthoquinone and 900 parts of ethylene glycol monomethylether is heated to 100° with stirring. A solution of 40 parts of isoquinoline in 100 parts of ethylene glycol monomethylether is added over a period of 20 minutes. Stirring is continued for 1 hour at reflux temperature. On cooling to about 100°, the precipitate is filtered, washed with ethylene glycol monomethylether, water and methanol and dried at 110°. The compound obtained is of the formula

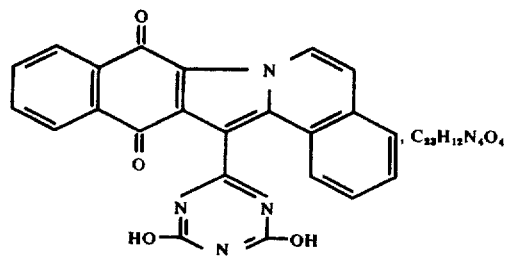, $C_{23}H_{12}N_4O_4$ which is verified by elementary analysis:

|  | C | H | N | O |
|---|---|---|---|---|
| Theory: | 67.6 | 3.0 | 13.7 | 15.7 |
| Found: | 67.3 | 3.1 | 13.9 | 15.6 |

The pigment thus obtained gives an orange dyeing.
4-Chloro-(4',6'-dihydroxy-1',3',5'-triazinyl)-acetylaminobenzene is produced in analogy with the operating procedure described in Example 1 for the production of the 2-chlorobenzene compound employing the corresponding 4-chloroanilide. Still in analogy with the said procedure, further compounds which are equally suitable for the production of the new dyes can be prepared. Those compounds may contain any one of the following radicals in place of the chlorophenylamino group: ethoxy-, tert. butoxy-, phenylamino, 2-methoxyphenylamino, 2,5-dimethoxyphenylamino, 2,5-dimethoxy-4-chlorophenylamino, 2,5-dimethoxy-4-bromophenylamino, 2-methylphenylamino, ethylamino, dimethylamino.

EXAMPLE 3

A mixture of 50.8 parts of iodine, 25 parts of 2,6-diamino-4-methyl-1,3,5-triazin and 250 parts of pyridine is raised to 100° and stirred for 2 hours. Over a period of 40 minutes, and at the same temperature, 45.4 parts of 2,3-dichloro-1,4-naphthoquinone are added and the reaction mixture is stirred for another 2 hours. The insoluble precipitate is isolated by filtration at 20°, washed with dimethyl formamide and subsequently washed with ethanol until the filtrate is colourless. The residue is then entered into 1000 parts of water in which it partly dissolves, raised to 100° and adjusted to pH 12 by gradual addition of sodium carbonate. The insoluble red pigment is isolated by filtration, washed with water until neutral and dried at 120° under vacuum. The pigment agrees with the formula

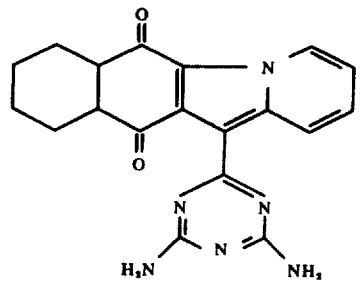

APPLICATION EXAMPLE A 0.2 Parts of the pigment obtained according to the procedure of Example 1 and 5 parts of titanium dioxide are intimately admixed with
63 parts polyvinyl chloride emulsion
32 parts di-octyl phthalate
3 parts epoxy plasticizer Reaplast 39 (Trade Mark)
1.5 parts standard stabilizer (barium cadmium complex) and
0.5 parts triphenylphosphite
by stirring, worked on a roller mill in which one roller is set to rotate at 20 r.p.m. and the other roller is set to rotate at 25 r.p.m., thus causing a frictional effect which in turn allows an extremely even pigment distribution to be obtained.

Finally the mixture is extruded as a film 0.3 mm thick which exhibits a blueish red shade.

The following table lists dyes of formula

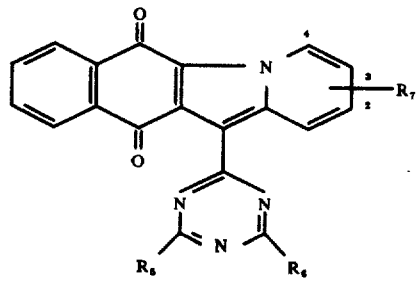

which are produced in analogy with the operating procedure of Examples 1, 2 or 3.

TABLE 1

| Ex. no. | $R_5$ | $R_6$ | $R_7$ | Shade in polyvinyl chloride |
|---|---|---|---|---|
| 4 | —OH | —OH | H | reddish violet |
| 5 | —OH | —OH | 2-CH₃ | " |
| 6 | —OH | —OH | 2-COOC₂H₅ | orange red |
| 7 | —OH | —OH | 2-COOCH₃ | " |
| 8 | —OH | —OH | 1- or 3--COOC₂H₅ | " |
| 9 | —OH | —OH | 2-CONHCH₃ | red |
| 10 | —OH | —OH | 1- or 3--CONH₂ | " |
| 11 | —OH | —OH | 2-CON(C₂H₅)₂ | " |
| 12 | —OH | —OH | 2-CONHC₆H₅ | " |
| 13 | —OH | —OH | 1- or 3--Cl | orange red |
| 14 | —OH | —OH | 1- or 3-Br | " |
| 15 | —N(CH₃)₂ | —N(CH₃)₂ | H | red |
| 16 | —NH—C₆H₅ | —NH—C₆H₅ | H | " |

TABLE 1-continued

| Ex. no. | $R_5$ | $R_6$ | $R_7$ | Shade in polyvinyl chloride |
|---|---|---|---|---|
| 17 | —NH—⟨C₆H₄⟩—Cl | —NH—⟨C₆H₄⟩—Cl | H | red |
| 18 | —OCH₃ | —OCH₃ | H | " |
| 19 | —OH | —OH | 1- or 3-CH₃ | " |
| 20 | —NH₂ | —NH₂ | 1- or 3-CH₃ | " |
| 21 | —NH₂ | —NH₂ | 2- —CH₃ | " |
| 22 | —N(CH₂CH₂OH)₂ | —N(CH₂CH₂OH)₂ | H | " |
| 23 | —NHC₂H₅ | —NHC₂H₅ | H | " |
| 24 | —NHCH₃ | —NHCH₃ | 1- or 3-Cl | " |
| 25 | —N(C₂H₅)₂ | —N(C₂H₅)₂ | " | " |
| 26 | —OH | —OH | 1- or 3--CONC₂H₅ | " |
| 27 | —OH | —OH | 1- or 3--CON(CH₃)₂ | " |

The dyes listed in Table 2 below can also be produced in analogy with the operating procedure of the Examples 1, 2 or 3. They agree with formula

TABLE 2

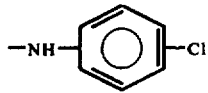

| Ex. no. | $R_5$ | $R_5'$ | $R_6'$ | $R_7$ | Shade in polyvinyl chloride |
|---|---|---|---|---|---|
| 28 | —OH | —OH | Cl | H | red |
| 29 | —OH | —OH | H | H | " |
| 30 | —OH | —OH | Cl | 2-CH₃ | " |
| 31 | —OH | —OH | Cl | 2-COOCH₃ | " |
| 32 | —OH | —OH | Cl | 1- or 3-CONH₂ | " |
| 33 | —NH₂ | —NH₂ | Cl | H | " |
| 34 | —NH₂ | —NH₂ | Br | 1- or 3-CH₃ | " |
| 35 | —NHCH₃ | —NHCH₃ | Cl | H | " |
| 36 | —OH | —OH | Cl | 2-CONHC₂H₅ | " |

In Examples 8, 10, 13, 14, 19, 20, 24, 26, 27, 32 and 34, isomeric mixtures are obtained, which mixtures may be separated.

What we claim is:

1. A compound of formula Ia,

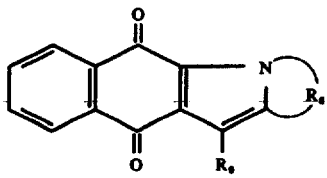

Ia wherein $R_8$ is a radical of formula P

—CH=CH—CH=CH—   P or a radical of formula Q

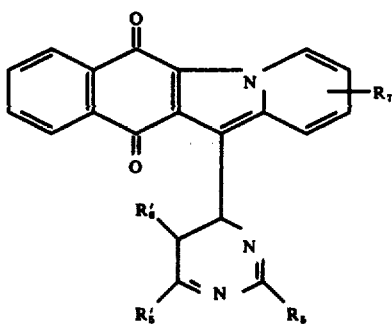

Q which radicals are unsubstituted or mono-substituted by chloro, bromo, methyl, methoxy, aminocarbonyl, methylaminocarbonyl, ethylaminocarbonyl, dimethylaminocarbonyl, diethylaminocarbonyl, phenylaminocarbonyl, methoxycarbonyl or ethoxycarbonyl, and $R_9$ is pyrimidyl or pyrimidyl substituted by up to three substituents selected from the group consisting of hydroxy, methoxy, ethoxy, amino, methylamino, ethylamino, dimethylamino, diethylamino, dihydroxyethylamino, phenylamino, chloro, bromo and mono-chlorophenylamino.

2. A compound according to claim 1, of the formula,

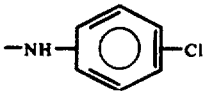

wherein
each of $R_5$, $R_5'$ and $R_6'$, independently, is hydrogen, chloro, bromo, hydroxy, amino or methylamino, with the proviso that at least one of $R_5$, $R_5'$ and $R_6'$ has a significance other than hydrogen, and
$R_7$ is hydrogen, methyl, methoxycarbonyl, aminocarbonyl or ethylaminocarbonyl.

3. A compound according to claim 1, in which $R_8$ is a radical of formula P.

4. A compound according to claim 1, in which $R_8$ is a radical of formula Q.

* * * * *